(12) United States Patent
Asakawa et al.

(10) Patent No.: US 8,551,916 B2
(45) Date of Patent: Oct. 8, 2013

(54) METHOD FOR PREPARATION OF AQUEOUS EMULSION USING INTERFACIALLY ACTIVE ORGANIC COMPOUND AS EMULSIFYING AGENT

(75) Inventors: Masumi Asakawa, Ibaraki (JP); Masaki Kogiso, Ibaraki (JP); Toshimi Shimizu, Ibaraki (JP); Atsushi Kisuno, Ibaraki (JP)

(73) Assignees: Hodogaya Chemical Co., Ltd., Tokyo (JP); National Institute of Advanced Insustrial Science and Technology, Tokyo (JP)

( * ) Notice: Subject to any disclaimer, the term of this patent is extended or adjusted under 35 U.S.C. 154(b) by 273 days.

(21) Appl. No.: 12/918,943

(22) PCT Filed: Feb. 25, 2009

(86) PCT No.: PCT/JP2009/053457
§ 371 (c)(1),
(2), (4) Date: Aug. 23, 2010

(87) PCT Pub. No.: WO2009/107683
PCT Pub. Date: Sep. 3, 2009

(65) Prior Publication Data
US 2011/0003695 A1     Jan. 6, 2011

(30) Foreign Application Priority Data

Feb. 25, 2008    (JP) ................. 2008-043426

(51) Int. Cl.
| | |
|---|---|
| *A01N 63/00* | (2006.01) |
| *A01N 37/00* | (2006.01) |
| *A01N 37/18* | (2006.01) |
| *A01N 47/10* | (2006.01) |
| *A61K 38/00* | (2006.01) |
| *A61K 31/27* | (2006.01) |

(52) U.S. Cl.
USPC ............ 504/118; 504/142; 504/149; 514/1.1; 514/479; 514/613

(58) Field of Classification Search
None
See application file for complete search history.

(56) References Cited

U.S. PATENT DOCUMENTS

| | | | |
|---|---|---|---|
| 5,492,696 A | 2/1996 | Price et al. | |
| 6,153,657 A * | 11/2000 | Kisuno et al. | ................ 424/401 |
| 2004/0120998 A1 | 6/2004 | Masuda et al. | |

FOREIGN PATENT DOCUMENTS

| | | |
|---|---|---|
| JP | 03-050279 | 3/1991 |
| JP | 3-207441 | 9/1991 |
| JP | 11-070733 | 3/1999 |
| JP | 11-172225 | 6/1999 |
| JP | 2001-055302 | 2/2001 |
| JP | 2002-080489 | 3/2002 |
| JP | 2002-129031 | 5/2002 |
| JP | 2002-322190 | 11/2002 |
| JP | 2002-363289 | 12/2002 |
| JP | 2003-221448 | 8/2003 |
| JP | 2003-259893 | 9/2003 |
| JP | 2004-224717 | 8/2004 |
| JP | 2004-250797 | 9/2004 |
| JP | 2004-261885 | 9/2004 |
| JP | 2006-072158 | 3/2006 |
| JP | 2006-143723 | 6/2006 |
| JP | 2007-181789 | 7/2007 |
| JP | 2007-289116 | 11/2007 |

OTHER PUBLICATIONS

Jung et al., "Self-Assembling Structures of Long-Chain Phenyl Glucoside Influenced by the Introduction of Double Bonds" *Journal of the American Chemical Society* vol. 124, No. 36, pp. 10674-10675, 2002.
Kamiya et al., "Molecular Structure of Glucopyranosylamide Lipid and Nanotube Morphology" *Langmuir* vol. 21, pp. 743-750, 2005.
International Search Report issued with respect to PCT/JP2009/053457, mailed May 12, 2009.
Toshimi Shimizu, "Self-Assembly in Discrete Organic Nanotubes, Japan", the society of fiber science and technology, Sent Gakkaishi, vol. 62, No. 4, Apr. 10, 2006, pp. 30-34.
Japan Office action, dated May 14, 2013 along with an english translation thereof.

\* cited by examiner

*Primary Examiner* — Alton Pryor
(74) *Attorney, Agent, or Firm* — Greenblum & Bernstein, P.L.C.

(57) ABSTRACT

The present invention provides a method for obtaining O/W emulsions by emulsifying various to-be-emulsified material without the use of any organic solvent, and drying and making into powder the O/W emulsion. The invention relates to a method for producing an O/W emulsion including after preliminarily dispersing a to-be-emulsified material and an interfacially active organic compound in water, heating the preliminary dispersion to a temperature equal to or higher than the melting point of the to-be-emulsified material and equal to or higher than the phase transition temperature of a self-assembled product of the interfacially active organic compound in the absence of an organic solvent, and performing emulsification under a pressure.

18 Claims, 5 Drawing Sheets

METHOD FOR PREPARATION OF AQUEOUS EMULSION USING INTERFACIALLY ACTIVE ORGANIC COMPOUND AS EMULSIFYING AGENT

TECHNICAL FIELD

The present invention relates to a method for subjecting an interfacially active organic compound and a to-be-emulsified material to O/W emulsification in water or an aqueous solvent by a high-temperature pressurization treatment, without requiring an organic solvent.

BACKGROUND ART

In the case of subjecting a to-be-emulsified material to O/W emulsification, it is necessary to use an organic solvent capable of dissolving the to-be-emulsified material therein to dissolve it. Also, in order to obtain a stable emulsion, it is necessary to select an appropriate surfactant as an emulsifying agent, taking into consideration physicochemical characteristics of an organic solvent solution of the to-be-emulsified material, and carry out emulsification.

For example, JP-A-3-50279 discloses an aqueous release agent which is characterized by comprising an aqueous dispersion of a long-chain alkyl graft polymer obtained by mixing and stirring an aqueous solution of a polyamine and an alkyl isocyanate in the presence of hexane, ethyl acetate or toluene, thereby allowing the mixture to react. Also, JP-A-11-172225 discloses a release agent obtained by emulsifying a reaction product of EVA and an alkyl isocyanate having from 8 to 30 carbon atoms with a petroleum based solvent or decyl alcohol and with a surfactant which is a combination of a surfactant having a high HLB and a surfactant having a low HLB. Also, JP-A-2002-363289 discloses a method for producing a polymer aqueous dispersion by emulsifying and dispersing a mixture of a dispersoid dissolved in toluene and a dispersion medium by injection under an injection pressure of $6.5 \times 10^7$ Pa or more. Furthermore, JP-A-2002-129031 discloses a polymer aqueous dispersion and a method for producing the same, in which a releasable polymer having a long-chain alkyl group having 8 or more carbon atoms is dissolved in toluene, and the solution is emulsified and dispersed in water using an emulsifying agent having at least one long-chain hydrocarbon group having 15 or more carbon atoms. Further, JP-A-2003-221448 discloses a method for producing a polymer aqueous dispersion, which is characterized by emulsifying and dispersing, in water, a toluene solution of a dispersoid containing a releasable polymer having a long-chain alkyl group having 8 or more carbon atoms, by an emulsifying agent which is a combination system of an ampholytic surfactant and a nonionic surfactant, to form a microemulsion having a volume average particle size of not more than 0.1 µm.

However, with respect to a to-be-emulsified material which is sparingly soluble in an organic solvent, or the like, it is difficult to prepare a stable emulsion thereof, and as the one and only method, there is a melt emulsification method for emulsifying a to-be-emulsified material together with a surfactant at a high temperature of the melting point of the to-be-emulsified material or higher. For example, JP-A-11-70733 discloses a method in which a color-developing agent is heated at the melting point thereof or higher in an airtight container to achieve emulsification, followed by coating the emulsion. It is necessary to note that diethyl maleate which is used in all of the working examples is actually able to function as an organic solvent that dissolves the color-developing agent. Also, in Example 2 only in which the emulsification is performed under a high-temperature condition as it is, the emulsification is performed under a high-temperature and high-pressure condition by a dissolver using a general surfactant such as sodium dodecylbenzenesulfonate and sodium lauryl sulfate. However, with such a simple stirring and mixing condition as the said condition, the surfactant foams by the highly rotating dissolver, so that it does not work for the emulsification of the to-be-emulsified material, making it impossible to stably form an emulsion. Thus, a doubt remains in its results. Also, JP-A-2001-55302 discloses a formation method in which a solid is continuously melted, a surfactant or a dispersant is added thereto, and the mixture is suspended in an airtight chamber under a high shear condition. However, prior to the shearing, a solvent flow of such a low temperature that crystallizes the solid in a molten state during retention within the chamber is made joined together. It cannot be considered that the emulsification is achieved in a state where the solid under a high temperature is thoroughly dissolved, and it is difficult to stably obtain an emulsion having a small particle size regardless of the kind of the to-be-emulsified material.

In this melt emulsification method, a high-temperature treatment at the melting point of the to-be-emulsified material or higher is generally required. In the case of high-melting point materials to be emulsified, the treatment temperature greatly exceeds 100° C., at which water boils at normal pressure. Thus, it is necessary to restrain boiling of water by means of considerable pressurization. It becomes necessary a method for producing an O/W emulsion using a dispersion method capable of stably performing emulsification under a high-temperature and high-pressure condition using an emulsifying agent which even when such a high-temperature and high-pressure treatment is performed, is able to form a stable emulsion without causing decomposition or the like, while avoiding physical disturbance. However, most of emulsifying agents have a phase transition temperature of from about 60 to 80° C. and a melting point of from about 50 to 60° C. at the utmost, and only methods for producing an O/W emulsion capable of forming a stable emulsion at such a temperature level or lower have been reported. With respect to the dispersion method, a production method of stably forming an O/W emulsion by combining a melted to-be-emulsified material with an emulsifying agent whose phase transition temperature or melting point is high has not been known yet. In the fields of pharmaceutical agents, cosmetics, resin materials and the like, aqueous preparations are desired from the standpoints of environmental responsiveness and safety, and a method for producing an emulsion substantially eliminating an organic solvent is demanded.

Also, in conventional emulsions, when moisture which functions as a dispersion medium vanishes, emulsion particles are fused each other. Therefore, the resulting product cannot be made into powder by drying or the like. For that reason, the coexistence with a large amount of water functioning as a dispersion medium is essential, and there are such problems that the weight becomes large unavoidably, and that with materials to be emulsified that are susceptible to hydrolysis, a problem arises in long-term storage. If an emulsified material can be dried and made into powder as it is and can be easily restored to an emulsion at the time of use as the case may be, such is advantageous in terms of transportation cost and long-term storage. Such an emulsion has been demanded.

Also, as examples of using an organic nanotube, JP-A-2004-261885 discloses a method for introducing a functional material into an organic nanotube composed of sugar and a hydrocarbon; and U.S. Pat. No. 5,492,696 discloses a method in which after freeze-drying a nanotube formed of a phospholipid, a functional material is introduced into the nanotube, thereby performing release control.

DISCLOSURE OF THE INVENTION

Problems that the Invention to Solve

The invention is to provide a method for producing an O/W emulsion by emulsifying a to-be-emulsified material having a melting point under a high-temperature pressurization condition by utilizing an interfacially active organic compound as an emulsifying agent without requiring any organic solvent, to obtain an O/W emulsion and powdering the O/W emulsion upon being dried.

Means for Carrying out the Problems

In order to solve the foregoing problems, the present inventors made extensive and intensive investigations. As a result, it has been found that (1) the molecule constituting an organic nanotube is an amphipathic molecule having both a portion which is readily soluble in water (hydrophilic segment) and a portion which is readily soluble in an oil (hydrophobic segment) in one molecule like a soap molecule, and is an interfacially active organic compound basically having a function as a surfactant; (2) the molecule spontaneously assembles (hereinafter referred to as "self-assembly") in water, to form a nanotube structure; (3) furthermore, the melting point of the interfacially active organic compound is 140° C. or higher, and the interfacially active organic compound stably exhibits an interfacially active effect even at a high temperature of its melting point or higher and (4) the phase transition temperature of the organic nanotube formed of the interfacially active organic compound is from 30° C. to 90° C., and when heated to this temperature or higher in water, the nanotube structure instantaneously causes a morphological change to a spherical vesicle structure, and furthermore, it has been found that taking advantage of this physicochemical characteristic, a stable O/W emulsion can be prepared by emulsifying a desired to-be-emulsified material in water using an interfacially active organic compound under a high-temperature pressurization condition without the use of any organic solvent. Also, it has been found that (5) an organic compound having a chemical structure close to the interfacially active organic compound that forms an organic nanotube forms a pseudo organic nanotube vesicle structure, and the organic compound has a similar emulsification effect which, however, is slightly inferior to that of the interfacially active organic compound that forms an organic nanotube (hereinafter, the interfacially active organic compound that forms an organic nanotube vesicle structure and the interfacially active organic compound that forms a pseudo organic nanotube vesicle structure are collectively referred to as "interfacially active organic compound"); that (6) furthermore, an emulsion produced using such an interfacially active organic compound is readily dried and made into powder by drying; and that (7) when the dried powder is again added and dispersed into water, it is immediately restored to an emulsion. The foregoing findings lead to accomplishment of the invention.

The present invention is constituted of the following contents.

(1) A method for producing an O/W emulsion comprising: after preliminarily dispersing a to-be-emulsified material and an interfacially active organic compound in water, heating the preliminary dispersion to a temperature equal to or higher than a melting point of the to-be-emulsified material and equal to or higher than a phase transition temperature of a self-assembled product of the interfacially active organic compound in the absence of an organic solvent; and performing emulsification under a pressure.

(2) The method for producing an O/W emulsion according to (1) above, wherein the interfacially active organic compound is used as an emulsifying agent for the emulsification of the to-be-emulsified material.

(3) The method for producing an O/W emulsion according to (1) or (2) above, wherein the interfacially active organic compound is an interfacially active organic compound having a hydrocarbon chain having from 6 to 50 carbon atoms and at least one hydrophilic group selected from the group consisting of a sugar chain, a peptide chain and a metal salt, and the hydrocarbon chain and the hydrophilic group are bonded directly or via an amide bond, an arylene group or an aryleneoxy group.

(4) The method for producing an O/W emulsion according to any one of (1) to (3) above, wherein the interfacially active organic compound is one or two or more members selected from the group consisting of 1-glucosamide-oleic acid, glycylglycine-lauric acid, glycylglycine-myristic acid, 2-glucosamide-lauric acid, 2-glucosamide-myristic acid, 2-glucosamide-oleic acid and 2-glucosamide-stearic acid.

(5) The method for producing an O/W emulsion according to any one of (1) to (4) above, wherein the interfacially active organic compound is 1-glucosamide-oleic acid.

(6) The method for producing an O/W emulsion according to (5) above, wherein the self-assembled product of the interfacially active organic compound comprises an organic nanotube having an inner pore diameter of 5 nm or more.

(7) The method for producing an O/W emulsion according to any one of (1) to (6) above, wherein at the time of the preliminary dispersing in water, the interfacially active organic compound comprises a mixture of a self-assembled product and a non-self-assembled product of the interfacially active organic compound.

(8) The method for producing an O/W emulsion according to any one of (1) to (6) above, wherein at the time of the preliminary dispersing in water, the interfacially active organic compound consists of a self-assembled product of the interfacially active organic compound.

(9) The method for producing an O/W emulsion according to any one of (1) to (6) above, wherein at the time of the preliminary dispersing in water, the interfacially active organic compound consists of a non-self-assembled product of the interfacially active organic compound.

(10) The method for producing an O/W emulsion according to any one of (1) to (9) above, wherein the emulsification is performed under a pressure of 0.01 MPa or higher and not higher than 300 MPa.

(11) The method for producing an O/W emulsion according to any one of (1) to (10) above, wherein the preliminary dispersion is performed at atmospheric pressure and at normal temperature.

(12) The method for producing an O/W emulsion according to any one of (1) to (11) above, wherein the to-be-emulsified material is a release agent, a toner, an agricultural chemical, a pharmaceutical agent, a cosmetic, a resin material or a food.

(13) An O/W emulsion produced by, after preliminarily dispersing a to-be-emulsified material and an interfacially active organic compound in water at atmospheric pressure and at normal temperature, heating the preliminary dispersion to a temperature equal to or higher than a melting point of the to-be-emulsified material and equal to or higher than a phase transition temperature of a self-assembled product of the interfacially active organic compound in the absence of an organic solvent, and performing emulsification under a pressure.

(14) The O/W emulsion according to (13) above, wherein the interfacially active organic compound is used as an emulsifying agent for the emulsification of the to-be-emulsified material.

(15) The O/W emulsion according to (13) or (14) above, wherein the interfacially active organic compound is an interfacially active organic compound having a hydrocarbon chain having from 6 to 50 carbon atoms and at least one hydrophilic group selected from the group consisting of a sugar chain, a peptide chain and a metal salt, and the hydrocarbon chain and the hydrophilic group are bonded directly or via an amide bond, an arylene group or an aryleneoxy group.

(16) The O/W emulsion according to any one of (13) to (15) above, wherein the interfacially active organic compound is one or two or more members selected from the group consisting of 1-glucosamide-oleic acid, glycylglycine-lauric acid, glycylglycine-myristic acid, 2-glucosamide-lauric acid, 2-glucosamide-myristic acid, 2-glucosamide-oleic acid and 2-glucosamide-stearic acid.

(17) The O/W emulsion according to any one of (13) to (16) above, wherein the interfacially active organic compound is 1-glucosamide-oleic acid.

(18) The O/W emulsion according to any one of (13) to (17) above, wherein the to-be-emulsified material is a release agent, a toner, an agricultural chemical, a pharmaceutical agent, a cosmetic, a resin material or a food.

(19) A dried emulsion obtained by drying the O/W emulsion according to (13) above, to make it into powder.

(20) An O/W emulsion obtained by dispersing the dried emulsion according to (19) above in water, to again form an O/W emulsion.

(21) A method for producing a dried emulsion comprising drying the O/W emulsion according to (13) above, to make it into powder.

(22) A method for producing an O/W emulsion comprising dispersing the dried emulsion according to (19) above in water, to again form an O/W emulsion.

Advantages of the Invention

The technique of the invention which emulsifies various to-be-emulsified material in water by utilizing an interfacially active organic compound as an emulsifying agent without the use of any organic solvent, or which dries and makes into powder the obtained emulsion can be used for various applications according to properties of the to-be-emulsified material. For example, by making an active ingredient such as a pharmaceutical agent, a cosmetic, an agricultural chemical, a resin material or the like into an aqueous emulsion, an enhancement in the human safety and a reduction in the environmental pollution can be drastically attempted. Also, by drying and making it into powder, it is possible to achieve long-term stable storage and a reduction in a transportation cost. Furthermore, in view of the fact that the powder is again restored to an emulsion upon being added into water, it is possible to easily prepare an emulsion of the to-be-emulsified material at any time. From those standpoints, it is possible to develop, into a new stage, a to-be-emulsified material which has not been able to be introduced for the reasons, for example, of being readily hydrolyzable or of requiring a large amount of water so that the weight becomes large.

BEST MODE FOR CARRYING OUT THE INVENTION

The invention is hereunder described in detail.

The to-be-emulsified material, which is subjected to emulsification in the invention, is not particularly limited so far as it has a melting point and is insoluble in water, inclusive of pharmaceutical agents, cosmetics, foods, agricultural chemicals, electronic materials, resin materials and the like, and may be appropriately selected depending upon the purpose. The concentration of the to-be-emulsified material may be appropriately set depending upon its characteristics and purposes. Even a material which is liquid at normal temperature may be used so far as it is insoluble in water and is capable of forming an interface with water.

The interfacially active organic compound used in the invention comprises a hydrophobic hydrocarbon group and a hydrophilic group and can be used as it is (in a non-self-assembled state). Also, it may be used as an emulsifying agent even in a state where at least partially self-assembling proceeds to form a (pseudo) organic nanotube. Also, even an interfacially active organic compound that is freeze-dried after forming a (pseudo) organic nanotube can be used. The hydrocarbon group is preferably a hydrocarbon chain having from 6 to 50 carbon atoms. The hydrocarbon group is preferably linear, and may be saturated or unsaturated. In the case where the hydrocarbon group is unsaturated, it is preferable that the hydrocarbon group has not more than three double bonds. The hydrophilic group is preferably at least one member selected from the group consisting of a sugar chain, a peptide and a metal salt. Such hydrophilic group and hydrocarbon group are bonded directly or via an amide bond, an arylene group or an aryleneoxy group.

The kind of the interfacially active organic compound is exemplified below, but is not particularly limited thereto.

(a) O-Glycoside type glycolipids having a structure represented by the following general formula:

[Chem. 1]

wherein G represents a sugar residue, and R represents a hydrocarbon having from 6 to 25 carbon atoms (these are also disclosed in JP-A-2002-80489 and JP-A-2003-259893).
(b) Unsymmetrical bolaamphiphiles represented by the following general formula:

R'—NHCO—(CH$_2$)$_n$—COOH wherein R' represents a residue of an aldopyranose from which a reducing terminal hydroxyl group is eliminated, and n represents from 6 to 20 (these are also disclosed in JP-A-2002-322190).
(c) N-Glycoside type glycolipids represented by the following general formula:

G'-NHCO—R"

wherein G' represents a sugar residue from which a hemiacetal hydroxyl group bonding to the anomer carbon atom of a sugar is eliminated, and R" represents an unsaturated hydrocarbon group having from 10 to 39 carbon atoms (these are also disclosed in JP-A-2004-224717).
(d) Compounds composed of a peptide lipid represented by the following general formula and a transition metal:

R'''—CO(NHCH$_2$CO)$_m$OH wherein R''' represents a hydrocarbon group having from 6 to 18 carbon atoms, and m represents an integer of from 1 to 3 (these are also disclosed in JP-A-2004-250797).

Of these interfacially active organic compounds, one or two or more members selected from the group consisting of 1-glucosamide-oleic acid, glycylglycine-lauric acid, glycylglycine-myristic acid, 2-glucosamide-lauric acid, 2-glucosamide-myristic acid, 2-glucosamide-oleic acid and 2-glucosamide-stearic acid are preferable. 1-Glucosamide-oleic acid which forms an organic nanotube is especially preferable.

In the case of an interfacially active organic compound that forms an organic nanotube, when dissolved in water under a specified condition as described below, it undergoes self-assembling to form an organic nanotube structure of a hollow structure. In the case of an interfacially active organic compound that forms a pseudo organic nanotube structure, it undergoes self-assembling under the same condition to form a pseudo organic nanotube structure. The (pseudo) organic nanotubes undergo, when being subjected to temperature elevation in water, a morphological change of from a (pseudo) nanotube structure to a spherical (pseudo) vesicle structure occurring at the respective inherent phase transition temperature and inversely, when being subjected to a temperature decrease, a morphological change of from a (pseudo) vesicle structure to a (pseudo) nanotube structure occurring at the respective phase transition temperature.

Next, the method for producing an O/W emulsion is described.

The desired to-be-emulsified material is made together with the interfacially active organic compound and emulsified in water. Prior to the emulsification, it is preferable to achieve addition and dispersion in water as uniformly as possible at normal temperature and at atmospheric pressure. For the purpose of achieving uniform dispersion in water, though the mixture may be dispersed using a usual stirrer or screw-type agitator, it is preferable to perform the dispersion by treating the mixture using a homogenizer at 3,000 rpm or more for a period of from 10 to 30 minutes from the aspect of enabling the dispersion within a short time. The temperature condition and pressurization condition during the emulsification may be appropriately selected according to physico-chemical characteristics of the to-be-emulsified material and the interfacially active organic compound. At that time, it is preferable to perform the emulsification using a high-pressure emulsification device capable of setting up the temperature condition and the pressurization condition.

It is necessary to set up the temperature condition at a temperature which is equal to or higher than the melting point of the to-be-emulsified material and equal to or higher than the phase transition temperature of a self-assembled product of the interfacially active organic compound. Though an upper limit value of the temperature condition is not particularly limited so far as it is a temperature at which the used interfacially active organic compound is not decomposed or lower, it is preferably not higher than 250° C. Even in the case where an interfacially active organic compound which has not undergone self-assembling at all is used as the emulsifying agent, it is necessary to similarly set up the temperature condition, taking into consideration the phase transition temperature of a self-assembled product of the interfacially active organic compound. With regard to interfacially active organic compounds that form a pseudo organic nanotube vesicle structure, the phase transition temperature of the self-assembled product thereof is also from 30° C. to 90° C., similarly to the case of interfacially active organic compounds that form an organic nanotube vesicle structure. When heated to the temperature condition and pressurized, the interfacially active organic compound forms a vesicle structure in the form of taking the to-be-emulsified material therein. In the case of an interfacially active organic compound that takes a pseudo vesicle structure, the structure of taking the to-be-emulsified material therein is more stable and becomes close to a vesicle structure. Thereafter, even when the interfacially active organic compound is cooled to reach a temperature lower than the phase transition temperature, the (pseudo) vesicle structure is stably kept without undergoing a structural transition to a (pseudo) organic nanotube, and the surface of the structure has hydrophilicity. As a result, a stable emulsion of the to-be-emulsified material is formed.

In the case where the temperature condition exceeds the boiling point of water at normal pressure, the pressurization condition must be set up at a high pressure at least to an extent such that boiling of water is restrained by elevating the boiling point of water. As other effects, the particle size of the emulsion can be controlled according to the pressure, and when a high pressure is applied, it is possible to make the particle size of the emulsion smaller, thereby obtaining a stable emulsion. Taking these points into consideration, it is preferable to perform the pressurization of from 0.01 MPa to 300 MPa, and it is especially preferable to perform the pressurization of from 0.1 to 200 MPa.

In the emulsification step of the invention, since a dispersoid containing the to-be-emulsified material and an aqueous dispersion medium containing the interfacially active organic compound are brought into mutual contact with each other as an ultra-high pressure and ultra-high speed fluid by the pressurization, the to-be-emulsified material can be dispersed as a fine particle with good storage stability in water. Further, since the mixture of the dispersoid and the aqueous dispersion medium is injected at an ultra-high pressure and at an ultra-high speed, it is possible to efficiently use high energy for the production of an aqueous dispersion, and a fine O/W emulsion having an average particle size of sub-microns or smaller can be obtained with a very small amount of the interfacially active organic compound.

In the method for producing an emulsion, an ionic surfactant and/or a nonionic surfactant may be added as an additive. The addition of such an additive is effective for more reducing the volume average particle size of the dispersed matter in the obtained emulsion and for improving the storage stability of the emulsion. Further, such is also effective for improving hydration properties and structure-forming properties of the interfacially active organic compound. However, there may be the case where a particular effect is not brought thereby depending upon the kind of the interfacially active organic compound used as the emulsifying agent.

In the present invention, as an instrument used for emulsifying the to-be-emulsified material using the interfacially active organic compound, a high-pressure emulsification device capable of regulating and setting up a pressure and a temperature is preferable. Specific examples thereof include an ultra-high pressure jet flow inversion type emulsifying and dispersing machine NANO3000 (manufactured by BeRyu Co., Ltd.), CLEAMIX/W-MOTION (manufactured by M Technique Co., Ltd.), NANO MAKER LSU-2010 (manufactured by Advanced Nano Technology Co., Ltd.), a wet type atomization unit STARBURST (manufactured by Sugino Machine Limited), BUPS-200 (manufactured by Yoshida Kikai Co., Ltd.) and MICROFLUIDIZER M-140k (manufactured by Mizuho Industrial Co., Ltd.).

After the emulsification and dispersion by the injection at an ultra-high pressure and at an ultra-high speed, a vacuum-heating treatment or the like may be performed, so that a desired emulsion can be formed thereby. Though the dry weight concentration of the obtained emulsion is not particularly limited, it is generally preferably from about 5 to 70% by weight, and especially preferably from 10 to 60% by weight.

Since the vesicle structure product in the emulsion is different from the conventional emulsion particles and, similarly to the organic nanotube, is high in physical stability and has characteristics like microcapsule, it can be made into powder by drying. Though the drying method is not particularly limited, the vesicle structure product may be filtered out by means of suction filtration or centrifuged to recover it as a precipitate, followed by drying by spontaneous drying and/or blowing moderate warm air. The dried powder of the vesicle structure product is stable over a long period as it is, and it can be easily restored to an emulsion when being added and dispersed into water again.

With respect to the condition under which the interfacially active organic compound undergoes self-assembling to form an organic nanotube, an example of its preparation condition is shown below. First of all, the interfacially active organic compound is dissolved in water to prepare a solution of the interfacially active organic compound. Examples of the water which is used herein include distilled water, purified water and ultra-pure water. The concentration of the interfacially active organic compound in the solvent is preferably from 0.001 w/v % to 0.02 w/v %. Subsequently, the solution is heated to a prescribed temperature (from 40 to 100° C.) and then cooled to a prescribed temperature (which is from a freezing temperature of the aqueous solution to 30° C.) at a prescribed cooling rate (not higher than 5° C./min), followed by allowing it to stand for a prescribed period of time (one day or longer) at that temperature. Though the size of the hollow organic nanotube formed by this step varies depending upon the condition, in general, its inner pore diameter is substantially 5 nm or larger, preferably not larger than 500 nm, and especially preferably from 10 nm to 200 nm; and its outer diameter is substantially not larger than 1,000 μm, and especially preferably from 50 to 300 nm. In the case of using an organic nanotube in the present invention, the ranges of the inner pore diameter and the outer diameter are not particularly specified.

In the case where it is intended to remove the moisture from the formed organic nanotube, the organic nanotube may be freeze-dried. Also, an organic nanotube in which an interfacially active organic compound in a non-self-assembled state is intermingled may be freeze-dried. The freezing temperature of the freeze-drying is preferably not higher than −70° C., and it is simple and easy to use liquid nitrogen. The degree of vacuum of the freeze-drying is preferably not more than 20 Pa, and more preferably not more than 1.0 Pa. The time of the freeze-drying is preferably 24 hours or more, and more preferably 72 hours or more.

The organic nanotube is structurally stable even in a dry state and can be dispersed again in water while keeping the structure.

The present invention will be illustrated with reference to the following Examples, but it should not be construed that the invention is limited thereto. Incidentally, in those Examples in which the term "organic nanotube" is not described, an interfacially active organic compound in a non-self-assembled state was used.

Example 1

[Release Agent]
1 g of an organic nanotube formed of 1-glucosamide-oleic acid (phase transition temperature: 70° C., melting point: 154° C.) and 5 g of polyvinyl octadecyl carbamate (melting point: 87 to 93° C.) as a to-be-emulsified material were suspended in 94 g of water.

Figure 1:
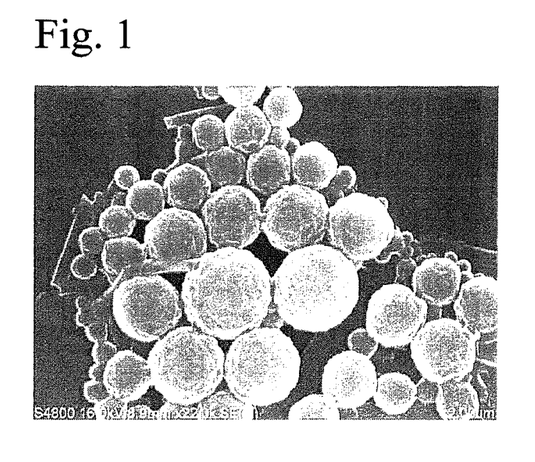
FIG. 1 is a view showing an SEM photograph of the O/W emulsion obtained in Example 1.

This suspension was subjected to a single-circulation treatment under the conditions of at 165° C. and 168 MPa using a high-pressure emulsification device NANO3000 (manufactured by BeRyu Co., Ltd.), thereby obtaining an O/W emulsion. The average particle size of this O/W emulsion was measured, and as a result, it was found to be 1.0 μm. The measurement conditions are as follows. 500 mg of the sample was suspended and dispersed in 50 mL of water, 1 mL of which was then taken out and introduced into MICROTRAC MT3300 (manufactured by Nikkiso Co., Ltd.). MICROTRAC MT3300 was set up at a particle refractive index of 1.81 and a solvent refractive index of 1.333 with the mode of volume distribution display, thereby measuring the average particle size. Furthermore, a photograph of the O/W emulsion was taken using an electron microscope. The result thereof is shown as FIG. 1. The measurement conditions are as follows. An appropriate amount of the sample was taken, dried on a graphite substrate and then observed and measured using an ultra-high resolution field emission scanning electron microscope S-4800 (manufactured by Hitachi High-Technologies Corporation).

The emulsion was subjected to suction filtration using a No. 5C filter paper (manufactured by Advantec Toyo Kaisha, Ltd.) to recover a vesicle structure product on the filter paper, and the vesicle structure product was air-dried for one day and then dried by warm air at 60° C. for 7 hours, thereby obtaining a powder.

Example 2

[Toner]
1 g of an organic nanotube formed of 1-glucosamide-oleic acid (phase transition temperature: 70° C., melting point:

154° C.) and 5 g of a polyester resin for toner (softening point: 140° C.) as a to-be-emulsified material were suspended in 94 g of water.

Figure 2:
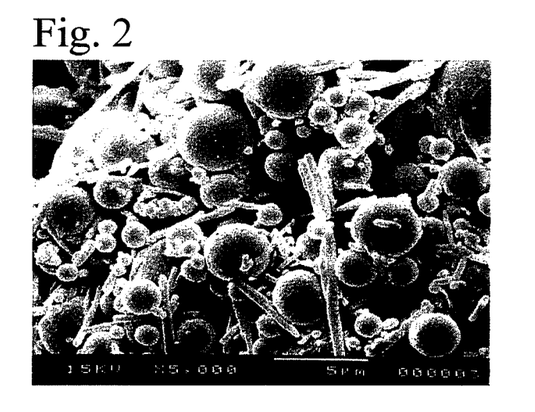
FIG. 2 is a view showing an SEM photograph of the O/W emulsion obtained in Example 2.

This suspension was subjected to a single-circulation treatment under the conditions of at 168° C. and 168 MPa using a high-pressure emulsification device NANO3000 (manufactured by BeRyu Co., Ltd.), thereby obtaining an O/W emulsion. The average particle size thereof was measured, and as a result, it was found to be 5.0 µm. The measurement conditions are the same as those in Example 1. Furthermore, a photograph of the O/W emulsion was taken using an electron microscope. The result thereof is shown as FIG. 2. The measurement conditions are the same as those in Example 1.

The emulsion was subjected to suction filtration using a No. 5C filter paper (manufactured by Advantec Toyo Kaisha, Ltd.) to recover a vesicle structure product on the filter paper, and the vesicle structure product was air-dried for one day and then dried by warm air at 60° C. for 7 hours, thereby obtaining a powder.

Example 3

[Agricultural Chemical]

1 g of an organic nanotube formed of 1-glucosamide-oleic acid (phase transition temperature: 70° C., melting point: 154° C.) and 5 g of a Chloro-IPC (melting point: 38 to 40° C.) as a to-be-emulsified material were suspended in 94 g of water.

Figure 3:
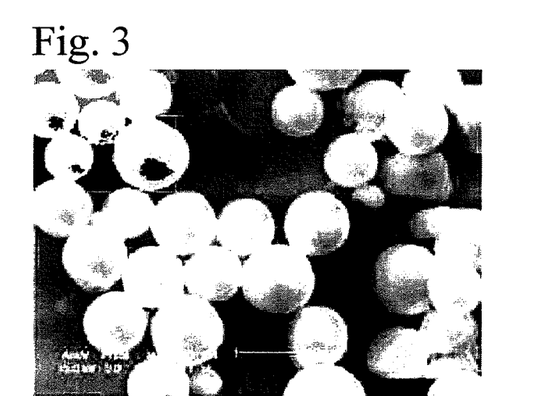
FIG. 3 is a view showing an SEM photograph of the O/W emulsion obtained in Example 3.

This suspension was subjected to a single-circulation treatment under the conditions of at 165° C. and 168 MPa using a high-pressure emulsification device NANO3000 (manufactured by BeRyu Co., Ltd.), thereby obtaining an O/W emulsion. The average particle size thereof was measured, and as a result, it was found to be 0.3 µm. The measurement conditions are the same as those in Example 1. Furthermore, a photograph of the O/W emulsion was taken using an electron microscope. The result thereof is shown as FIG. 3. The measurement conditions are the same as those in Example 1.

The emulsion was subjected to suction filtration using a No. 5C filter paper (manufactured by Advantec Toyo Kaisha, Ltd.) to recover a vesicle structure product on the filter paper, and the vesicle structure product was air-dried for one day and then dried by warm air at 60° C. for 7 hours, thereby obtaining a powder.

Example 4

[Agricultural Chemical (Phase Transition Temperature Treatment)]

1 g of an organic nanotube formed of 1-glucosamide-oleic acid (phase transition temperature: 70° C., melting point: 154° C.) and 5 g of a Chloro-IPC (melting point: 38 to 40° C.) as a to-be-emulsified material were suspended in 94 g of water.

This suspension was subjected to a single-circulation treatment under the conditions of at 70° C. and 0.01 MPa using a high-pressure emulsification device NANO3000 (manufactured by BeRyu Co., Ltd.), thereby obtaining an O/W emulsion. The average particle size thereof was measured, and as a result, it was found to be 3.0 µm. The measurement conditions are the same as those in Example 1.

The emulsion was subjected to suction filtration using a No. 5C filter paper (manufactured by Advantec Toyo Kaisha, Ltd.) to recover a vesicle structure product on the filter paper, and the vesicle structure product was air-dried for one day and then dried by warm air at 60° C. for 7 hours, thereby obtaining a powder.

Example 5

[Release Agent]

1 g of 1-glucosamide-oleic acid (phase transition temperature: 70° C., melting point: 154° C.) and 5 g of polyvinyl octadecyl carbamate (melting point: 87 to 93° C.) as a to-be-emulsified material were suspended in 94 g of water.

Figure 4:
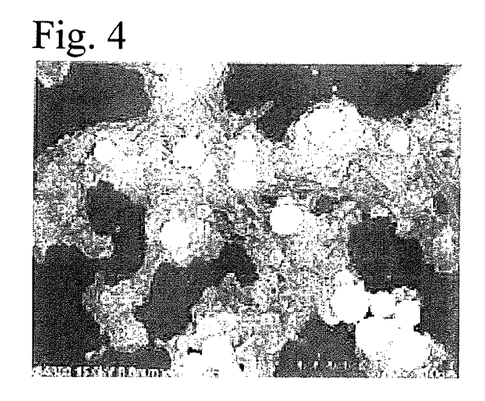
FIG. 4 is a view showing an SEM photograph of the O/W emulsion obtained in Example 5.

This suspension was subjected to a single-circulation treatment under the conditions of at 165° C. and 168 MPa using a high-pressure emulsification device NANO3000 (manufactured by BeRyu Co., Ltd.), thereby obtaining an O/W emulsion. The average particle size thereof was measured, and as a result, it was found to be 1.0 µm. The measurement conditions are the same as those in Example 1. Furthermore, a photograph of the O/W emulsion was taken using an electron microscope. The result thereof is shown as FIG. 4. The measurement conditions are the same as those in Example 1.

The emulsion was subjected to suction filtration using a No. 5C filter paper (manufactured by Advantec Toyo Kaisha, Ltd.) to recover a vesicle structure product on the filter paper, and the vesicle structure product was air-dried for one day and then dried by warm air at 60° C. for 7 hours, thereby obtaining a powder.

Example 6

[Toner]

1 g of 1-glucosamide-oleic acid (phase transition temperature: 70° C., melting point: 154° C.) and 5 g of a polyester resin for toner (softening point: 140° C.) as a to-be-emulsified material were suspended in 94 g of water.

This suspension was subjected to a single-circulation treatment under the conditions of at 165° C. and 168 MPa using a high-pressure emulsification device NANO3000 (manufactured by BeRyu Co., Ltd.), thereby obtaining an O/W emulsion. The average particle size thereof was measured, and as a result, it was found to be 5.0 µm. The measurement conditions are the same as those in Example 1.

The emulsion was subjected to suction filtration using a No. 5C filter paper (manufactured by Advantec Toyo Kaisha, Ltd.) to recover a vesicle structure product on the filter paper, and the vesicle structure product was air-dried for one day and then dried by warm air at 60° C. for 7 hours, thereby obtaining a powder.

Example 7

[Agricultural Chemical]

1 g of 1-glucosamide-oleic acid (phase transition temperature: 70° C., melting point: 154° C.) and 5 g of a Chloro-IPC (melting point: 38 to 40° C.) as a to-be-emulsified material were suspended in 94 g of water.

This suspension was subjected to a single-circulation treatment under the conditions of at 165° C. and 168 MPa using a high-pressure emulsification device NANO3000 (manufactured by BeRyu Co., Ltd.), thereby obtaining an O/W emulsion. The average particle size thereof was measured, and as a result, it was found to be 0.3 µm. The measurement conditions are the same as that in Example 1.

The emulsion was subjected to suction filtration using a No. 5C filter paper (manufactured by Advantec Toyo Kaisha, Ltd.) to recover a vesicle structure product on the filter paper, and the vesicle structure product was air-dried for one day and then dried by warm air at 60° C. for 7 hours, thereby obtaining a powder.

Example 8

[Agricultural Chemical (Phase Transition Temperature Treatment)]

1 g of 1-glucosamide-oleic acid (phase transition temperature: 70° C., melting point: 154° C.) and 5 g of a Chloro-IPC as a material (melting point: 38 to 40° C.) to be emulsified were suspended in 94 g of water.

This suspension was subjected to a single-circulation treatment under the conditions of at 70° C. and 0.01 MPa using a high-pressure emulsification device NANO3000 (manufactured by BeRyu Co., Ltd.), thereby obtaining an O/W emulsion. The average particle size thereof was measured, and as a result, it was found to be 3.0 µm. The measurement conditions are the same as those in Example 1.

The emulsion was subjected to suction filtration using a No. 5C filter paper (manufactured by Advantec Toyo Kaisha, Ltd.) to recover a vesicle structure product on the filter paper, and the vesicle structure product was air-dried for one day and then dried by warm air at 60° C. for 7 hours, thereby obtaining a powder.

Example 9

[Release Agent]

1 g of an 8/1 (weight ratio) mixture of: an organic nanotube formed of 1-glucosamide-oleic acid (phase transition temperature: 70° C., melting point: 154° C.); and 1-glucosamide-oleic acid, and 5 g of polyvinyl octadecyl carbamate (melting point: 87 to 93° C.) as a to-be-emulsified material were suspended in 94 g of water.

This suspension was subjected to a single-circulation treatment under the conditions of at 165° C. and 168 MPa using a high-pressure emulsification device NANO3000 (manufactured by BeRyu Co., Ltd.), thereby obtaining an O/W emulsion. The average particle size thereof was measured, and as a result, it was found to be 1.0 µm. The measurement conditions are the same as those in Example 1.

The emulsion was subjected to suction filtration using a No. 5C filter paper (manufactured by Advantec Toyo Kaisha, Ltd.) to recover a vesicle structure product on the filter paper, and the vesicle structure product was air-dried for one day and then dried by warm air at 60° C. for 7 hours, thereby obtaining a powder.

Example 10

[Toner]

1 g of an 8/1 (weight ratio) mixture of: an organic nanotube formed of 1-glucosamide-oleic acid (phase transition temperature: 70° C., melting point: 154° C.); and 1-glucosamide-oleic acid, and 5 g of a polyester resin for toner (softening point: 140° C.) as a to-be-emulsified material were suspended in 94 g of water.

This suspension was subjected to a single-circulation treatment under the conditions of at 168° C. and 168 MPa using a high-pressure emulsification device NANO3000 (manufactured by BeRyu Co., Ltd.), thereby obtaining an O/W emulsion. The average particle size thereof was measured, and as a result, it was found to be 5.0 µm. The measurement conditions are the same as those in Example 1.

The emulsion was subjected to suction filtration using a No. 5C filter paper (manufactured by Advantec Toyo Kaisha, Ltd.) to recover a vesicle structure product on the filter paper, and the vesicle structure product was air-dried for one day and then dried by warm air at 60° C. for 7 hours, thereby obtaining a powder.

Example 11

[Agricultural Chemical]

1 g of an 8/1 (weight ratio) mixture of: an organic nanotube formed of 1-glucosamide-oleic acid (phase transition temperature: 70° C., melting point: 154° C.); and 1-glucosamide-oleic acid, and 5 g of a Chloro-IPC (melting point: 38 to 40° C.) as a to-be-emulsified material were suspended in 94 g of water.

This suspension was subjected to a single-circulation treatment under the conditions of at 165° C. and 168 MPa using a high-pressure emulsification device NANO3000 (manufactured by BeRyu Co., Ltd.), thereby obtaining an O/W emulsion. The average particle size thereof was measured, and as a result, it was found to be 0.3 µm. The measurement conditions are the same as those in Example 1.

The emulsion was subjected to suction filtration using a No. 5C filter paper (manufactured by Advantec Toyo Kaisha, Ltd.) to recover a vesicle structure product on the filter paper, and the vesicle structure product was air-dried for one day and then dried by warm air at 60° C. for 7 hours, thereby obtaining a powder.

Example 12

[Agricultural Chemical (Phase Transition Temperature Treatment)]

1 g of an 8/1 (weight ratio) mixture of: an organic nanotube formed of 1-glucosamide-oleic acid (phase transition temperature: 70° C., melting point: 154° C.); and 1-glucosamide-oleic acid, and 5 g of a Chloro-IPC (melting point: 38 to 40° C.) as a to-be-emulsified material were suspended in 94 g of water.

This suspension was subjected to a single-circulation treatment under the conditions of at 70° C. and 0.01 MPa using a high-pressure emulsification device NANO3000 (manufactured by BeRyu Co., Ltd.), thereby obtaining an O/W emulsion. The average particle size thereof was measured, and as a result, it was found to be 3.0 µm. The measurement conditions are the same as those in Example 1.

The emulsion was subjected to suction filtration using a No. 5C filter paper (manufactured by Advantec Toyo Kaisha, Ltd.) to recover a vesicle structure product on the filter paper, and the vesicle structure product was air-dried for one day and then dried by warm air at 60° C. for 7 hours, thereby obtaining a powder.

Example 13

[Release Agent]

1 g of glycylglycine-lauric acid (MAM-1) (phase transition temperature: 49° C., melting point: 162° C.), 5 g of polyvinyl octadecyl carbamate (melting point: 87 to 93° C.) as a to-be-emulsified material and 0.1 g of a polyoxyethylene alkyl phenyl ether were suspended in 93.9 g of water.

Figure 5:
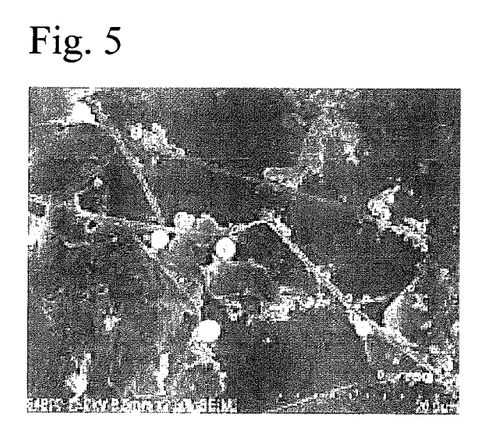
FIG. 5 is a view showing an SEM photograph of the O/W emulsion obtained in Example 13.

This suspension was subjected to a single-circulation treatment under the conditions of at 165° C. and 168 MPa using a high-pressure emulsification device NANO3000 (manufactured by BeRyu Co., Ltd.), thereby obtaining an O/W emulsion. The average particle size thereof was measured, and as a result, it was found to be 1.0 µm. The measurement conditions are the same as those in Example 1. Furthermore, a photograph of the O/W emulsion was taken using an electron microscope. The result thereof is shown as FIG. 5. The measurement conditions are the same as those in Example 1. The emulsion-formation efficiency was inferior to the formation efficiency in the case of using the organic nano-tube formed of 1-glucosamide-oleic acid and/or 1-glucosamide-oleic acid in a non-self-assembled state.

Example 14

[Release Agent]

1 g of glycylglycine-myristic acid (MAM-2) (phase transition temperature: 60° C., melting point: 159° C.), 5 g of polyvinyl octadecyl carbamate (melting point: 87 to 93° C.) as a to-be-emulsified material and 0.1 g of a polyoxyethylene alkyl phenyl ether were suspended in 93.9 g of water.

Figure 6:
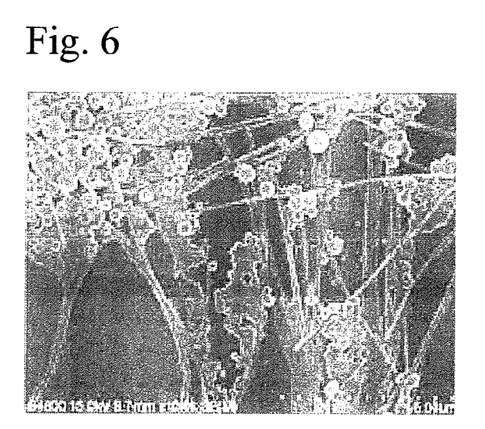
FIG. 6 is a view showing an SEM photograph of the O/W emulsion obtained in Example 14.

This suspension was subjected to a single-circulation treatment under the conditions of at 165° C. and 168 MPa using a high-pressure emulsification device NANO3000 (manufactured by BeRyu Co., Ltd.), thereby obtaining an O/W emulsion. The average particle size thereof was measured, and as a result, it was found to be 1.0 μm. The measurement conditions are the same as those in Example 1. Furthermore, a photograph of the O/W emulsion was taken using an electron microscope. The result thereof is shown as FIG. 6. The measurement conditions are the same as those in Example 1. The emulsion-formation efficiency was inferior to the formation efficiency in the case of using the organic nanotube formed of 1-glucosamide-oleic acid and/or 1-glucosamide-oleic acid in a non-self-assembled state.

Example 15

[Release Agent]

1 g of 2-glucosamide-lauric acid (GAM-1) (melting point: 208° C.), 5 g of polyvinyl octadecyl carbamate (melting point: 87 to 93° C.) as a to-be-emulsified material and 0.1 g of a polyoxyethylene alkyl phenyl ether were suspended in 93.9 g of water.

Figure 7:
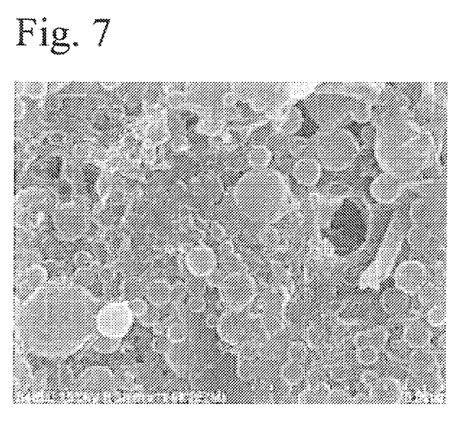
FIG. 7 is a view showing an SEM photograph of the O/W emulsion obtained in Example 15.

This suspension was subjected to a single-circulation treatment under the conditions of at 165° C. and 168 MPa using a high-pressure emulsification device NANO3000 (manufactured by BeRyu Co., Ltd.), thereby obtaining an O/W emulsion. The average particle size thereof was measured, and as a result, it was found to be 1.0 μm. The measurement conditions are the same as those in Example 1. Furthermore, a photograph of the O/W emulsion was taken using an electron microscope. The result thereof is shown as FIG. 7. The measurement conditions are the same as those in Example 1. Though the emulsion-formation efficiency was more excellent than the formation efficiency in the case of using MAM-1 or MAM-2, it was inferior to the formation efficiency in the case of using the organic nanotube formed of 1-glucosamide-oleic acid and/or 1-glucosamide-oleic acid in a non-self-assembled state.

Example 16

[Release Agent]

1 g of 2-glucosamide-myristic acid (GAM-2) (melting point: 198° C.), 5 g of polyvinyl octadecyl carbamate (melting point: 87 to 93° C.) as a to-be-emulsified material and 0.1 g of a polyoxyethylene alkyl phenyl ether were suspended in 93.9 g of water.

Figure 8:
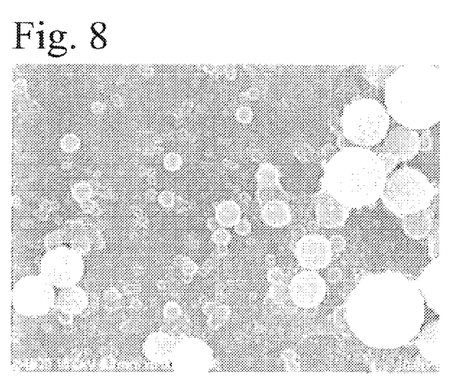
FIG. 8 is a view showing an SEM photograph of the O/W emulsion obtained in Example 16.

This suspension was subjected to a single-circulation treatment under the conditions of at 165° C. and 168 MPa using a high-pressure emulsification device NANO3000 (manufactured by BeRyu Co., Ltd.), thereby obtaining an O/W emulsion. The average particle size thereof was measured, and as a result, it was found to be 1.0 μm. The measurement conditions are the same as those in Example 1. Furthermore, a photograph of the O/W emulsion was taken using an electron microscope. The result thereof is shown as FIG. 8. The measurement conditions are the same as those in Example 1. Though the emulsion-formation efficiency was more excellent than the formation efficiency in the case of using MAM-1 or MAM-2, it was inferior to the formation efficiency in the case of using the organic nanotube formed of 1-glucosamide-oleic acid and/or 1-glucosamide-oleic acid in a non-self-assembled state.

Example 17

[Release Agent]

1 g of 2-glucosamide-oleic acid (GAM-3) (melting point: 159° C.), 5 g of polyvinyl octadecyl carbamate (melting point: 87 to 93° C.) as a to-be-emulsified material and 0.1 g of a polyoxyethylene alkyl phenyl ether were suspended in 93.9 g of water.

Figure 9:
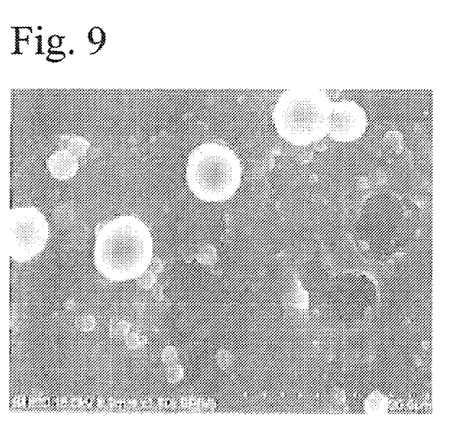
FIG. 9 is a view showing an SEM photograph of the O/W emulsion obtained in Example 17.

This suspension was subjected to a single-circulation treatment under the conditions of at 165° C. and 168 MPa using a high-pressure emulsification device NANO3000 (manufactured by BeRyu Co., Ltd.), thereby obtaining an O/W emulsion. The average particle size thereof was measured, and as a result, it was found to be 1.0 μm. The measurement conditions are the same as those in Example 1. Furthermore, a photograph of the O/W emulsion was taken using an electron microscope. The result thereof is shown as FIG. 9. The measurement conditions are the same as those in Example 1. Though the emulsion-formation efficiency was more excellent than the formation efficiency in the case of using MAM-1 or MAM-2, it was inferior to the formation efficiency in the case of using the organic nanotube formed of 1-glucosamide-oleic acid and/or 1-glucosamide-oleic acid in a non-self-assembled state.

Example 18

[Release Agent]

1 g of 2-glucosamide-stearic acid (GAM-4) (melting point: 194° C.), 5 g of polyvinyl octadecyl carbamate (melting point: 87 to 93° C.) as a to-be-emulsified material and 0.1 g of a polyoxyethylene alkyl phenyl ether were suspended in 93.9 g of water.

Figure 10:
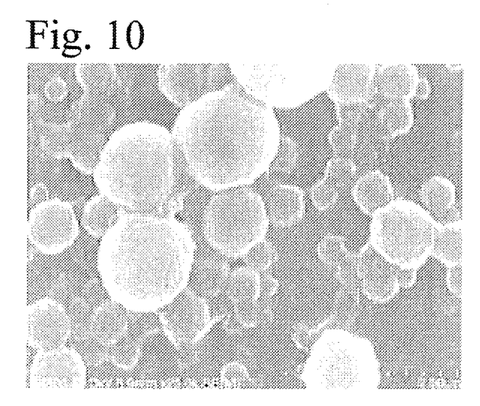
FIG. 10 is a view showing an SEM photograph of the O/W emulsion obtained in Example 18.

This suspension was subjected to a single-circulation treatment under the conditions of at 165° C. and 168 MPa using a high-pressure emulsification device NANO3000 (manufactured by BeRyu Co., Ltd.), thereby obtaining an O/W emulsion. The average particle size thereof was measured, and as a result, it was found to be 1.0 μm. The measurement conditions are the same as those in Example 1. Furthermore, a photograph of the O/W emulsion was taken using an electron microscope. The result thereof is shown as FIG. 10. The measurement conditions are the same as those in Example 1. Though the emulsion-formation efficiency was more excellent than the formation efficiency in the case of using MAM-1 or MAM-2, it was inferior to the formation efficiency in the case of using the organic nanotube formed of 1-glucosamide-oleic acid and/or 1-glucosamide-oleic acid in a non-self-assembled state.

Example 19

[Resuspension of Dried Emulsion]

500 mg of the dried emulsion of Chloro-IPC obtained in Example 4 was added in 100 mL of water, and the mixture was manually stirred and dispersed using a stirring rod, thereby obtaining an O/W emulsion. The average particle size thereof was measured, and as a result, it was found to be 3.0 µm. This result was equivalent to that measured before drying to obtain a powder in Example 4. The measurement conditions are the same as those in Example 1. This result revealed that the dried emulsion of Chloro-IPC was easily dispersed in water and restored to the original O/W emulsion.

Comparative Example 1

[Soybean Oil]

1 g of an organic nanotube formed of 1-glucosamide-oleic acid (phase transition temperature: 70° C., melting point: 154° C.) and 1 g of soybean oil (liquid at room temperature) as a to-be-emulsified material were suspended in 98 g of water.

Figure 11:
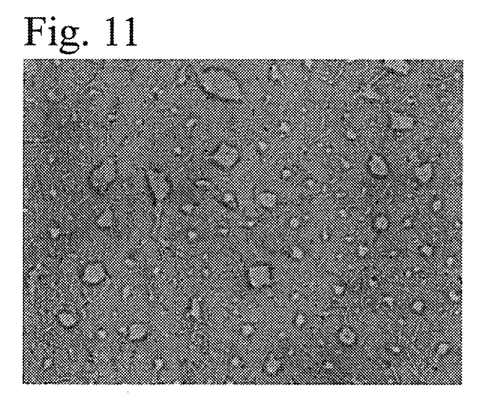
FIG. 11 is a view showing a digital microscope photograph of the suspension after treatment by NANO3000, as obtained in Comparative Example 1.

This suspension was subjected to a single-circulation treatment under the conditions of at room temperature and 168 MPa using a high-pressure emulsification device NANO3000 (manufactured by BeRyu Co., Ltd.). However, an emulsion owing to a vesicle structure was not obtained, and a state where the organic nanotube was attached to the surroundings of oil droplets of the soybean oil was observed. The result of taking a photograph using a digital microscope VHX-100 (manufactured by Keyence Corporation) installed with a zoom lens VH-Z450 (manufactured by Keyence Corporation) is shown as FIG. 11.

Comparative Example 2

[Release Agent]

1 g of RUNOX 1000C (melting point: 150° C.) (manufactured by Toho Chemical Industry Co., Ltd.) and 5 g of polyvinyl octadecyl carbamate (melting point: 87 to 93° C.) as a to-be-emulsified material were suspended in 94 g of water.

Figure 12:
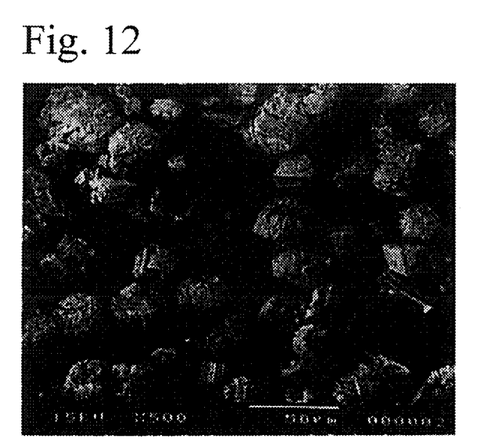
FIG. 12 is a view showing an SEM photograph of the suspension after treatment by NANO3000, as obtained in Comparative Example 2.

This suspension was subjected to a single-circulation treatment under the conditions of at 165° C. and 168 MPa using a high-pressure emulsification device NANO3000 (manufactured by BeRyu Co., Ltd.). However, an emulsion was not obtained. The result of taking a photograph using an electron microscope is shown as FIG. 12. The measurement conditions are the same as those in Example 1.

Comparative Example 3

[Release Agent]

1 g of SORPOL 5115 (melting point: 150° C.) (manufactured by Toho Chemical Industry Co., Ltd.) and 5 g of polyvinyl octadecyl carbamate (melting point: 87 to 93° C.) as a to-be-emulsified material were suspended in 94 g of water.

Figure 13:
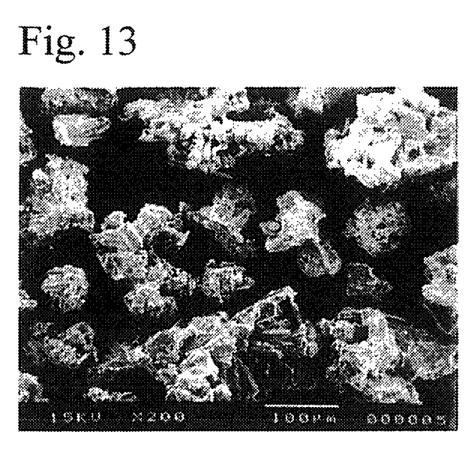
FIG. 13 is a view showing an SEM photograph of the suspension after treatment by NANO3000, as obtained in Comparative Example 3.

This suspension was subjected to a single-circulation treatment under the conditions of at 165° C. and 168 MPa using a high-pressure emulsification device NANO3000 (manufactured by BeRyu Co., Ltd.). However, an emulsion was not obtained. The result of taking a photograph using an electron microscope is shown in FIG. 13. The measurement conditions are the same as those in Example 1.

While the invention has been described in detail and with reference to specific embodiments thereof, it will be apparent to one skilled in the art that various changes and modifications can be made therein without departing from the spirit and scope thereof.

This application is based on Japanese Patent Application No. 2008-043426, filed Feb. 25, 2008, the entire contents of which are herein incorporated by reference.

INDUSTRIAL APPLICABILITY

The technique of the invention which emulsifies various to-be-emulsified material in water by utilizing an interfacially active organic compound as an emulsifying agent without the use of any organic solvent, or which dries and makes into powder the obtained emulsion can be used for various applications according to properties of the to-be-emulsified material. For example, by making an active ingredient such as a pharmaceutical agent, a cosmetic, an agricultural chemical, a resin material or the like into an aqueous emulsion, an enhancement in the human safety and a reduction in the environmental pollution can be drastically attempted. Also, by drying and making it into powder, it is possible to achieve long-term stable storage and a reduction in a transportation cost. Furthermore, in view of the fact that the powder is again restored to an emulsion upon being added into water, it is possible to easily prepare an emulsion of the to-be-emulsified material at any time. From those standpoints, it is possible to develop, into a new stage, a to-be-emulsified material which has not been able to be introduced for the reasons, for example, of being readily hydrolyzable or of requiring a large amount of water so that the weight becomes large.

The invention claimed is:

1. A method for producing an O/W emulsion comprising: after preliminarily dispersing a to-be-emulsified material and an interfacially active organic compound comprising a self-assembled product thereof in water, heating the preliminary dispersion to a temperature equal to or higher than a melting point of the to-be-emulsified material and equal to or higher than a phase transition temperature of the self-assembled product of the interfacially active organic compound in the absence of an organic solvent; and performing emulsification under a pressure; wherein the self-assembled product of the interfacially active organic compound comprises an organic nanotube, and wherein the interfacially active organic compound is one or more members selected from the group consisting of 1-glucosamide-oleic acid, glycylglycine-lauric acid, glycylglycine-myristic acid, 2-glucosamide-lauric acid, 2-glucosamide-myristic acid, 2-glucosamide-oleic acid, and 2-glucosamide-stearic acid.

2. The method for producing an O/W emulsion according to claim 1, wherein the interfacially active organic compound is used as an emulsifying agent for the emulsification of the to-be-emulsified material.

3. The method for producing an O/W emulsion according to claim 1, wherein the interfacially active organic compound is 1-glucosamide-oleic acid.

4. The method for producing an O/W emulsion according to claim 3, wherein the organic nanotube has an inner pore diameter of 5 nm or more.

5. The method for producing an O/W emulsion according to claim 1, wherein at the time of the preliminary dispersing in water, the interfacially active organic compound comprises a mixture of a self-assembled product and a non-self-assembled product of the interfacially active organic compound.

6. The method for producing an O/W emulsion according to claim 1, wherein at the time of the preliminary dispersing in water, the interfacially active organic compound consists of a self-assembled product of the interfacially active organic compound.

7. The method for producing an O/W emulsion according to claim 1, wherein at the time of the preliminary dispersing in water, the interfacially active organic compound consists of a non-self-assembled product of the interfacially active organic compound.

8. The method for producing an O/W emulsion according to claim 1, wherein the emulsification is performed under a pressure of 0.01 MPa or higher and not higher than 300 MPa.

9. The method for producing an O/W emulsion according to claim 1, wherein the preliminary dispersion is performed at atmospheric pressure.

10. The method for producing an O/W emulsion according to claim 1, wherein the to-be-emulsified material is a release agent, a toner, an agricultural chemical, a pharmaceutical agent, a cosmetic, a resin material or a food.

11. An O/W emulsion produced by, after preliminarily dispersing a to-be-emulsified material and an interfacially active organic compound in water at atmospheric pressure, heating the preliminary dispersion to a temperature equal to or higher than a melting point of the to-be-emulsified material and equal to or higher than a phase transition temperature of a self-assembled product of the interfacially active organic compound in the absence of an organic solvent, and performing emulsification under a pressure; wherein the self-assembled product of the interfacially active organic compound comprises an organic nanotube, and wherein the interfacially active organic compound is one or more members selected from the group consisting of 1-glucosamide-oleic acid, glycylglycine-lauric acid, glycylglycine-myristic acid, 2-glucosamide-lauric acid, 2-glucosamide-myristic acid, 2-glucosamide-oleic acid, and 2-glucosamide-stearic acid.

12. The O/W emulsion according to claim 11, wherein the interfacially active organic compound is used as an emulsifying agent for the emulsification of the to-be-emulsified material.

13. The O/W emulsion according to claim 11, wherein the interfacially active organic compound is 1-glucosamide-oleic acid.

14. The O/W emulsion according to claim 11, wherein the to-be-emulsified material is a release agent, a toner, an agricultural chemical, a pharmaceutical agent, a cosmetic, a resin material or a food.

15. A dried emulsion obtained by drying the O/W emulsion according to claim 11, to make it into powder.

16. An O/W emulsion obtained by dispersing the dried emulsion according to claim 15 in water, to again form an O/W emulsion.

17. A method for producing a dried emulsion comprising drying the O/W emulsion according to claim 11, to make it into powder.

18. A method for producing an O/W emulsion comprising dispersing the dried emulsion according to claim 15 in water, to again form an O/W emulsion.

* * * * *